United States Patent [19]
Korte et al.

[11] Patent Number: 4,772,728
[45] Date of Patent: Sep. 20, 1988

[54] METHOD FOR MAKING BICYCLIC LACTONES FROM BETA, GAMMA UNSATURATED CYCLIC NITRILES

[75] Inventors: Stephan Korte; Craig W. Coulston, both of Alamogordo; Friedhelm Korte, Attenkirchen, all of Fed. Rep. of Germany

[73] Assignee: Angus Chemical Company, Northbrook, Ill.

[21] Appl. No.: 767,165

[22] Filed: Aug. 19, 1985

[51] Int. Cl.$^4$ ............................................. C07D 311/76
[52] U.S. Cl. .................................... 549/290; 549/283; 549/311; 549/302
[58] Field of Search ................. 549/283, 311, 302, 290

[56] References Cited

U.S. PATENT DOCUMENTS

| | | | |
|---|---|---|---|
| 3,480,634 | 11/1969 | Finkelstein et al. | 549/290 |
| 3,936,473 | 2/1976 | Symon et al. | 549/290 |
| 4,219,449 | 8/1980 | Lenselink et al. | 252/522 R |

FOREIGN PATENT DOCUMENTS

| | | | |
|---|---|---|---|
| 1180759 | 11/1964 | Fed. Rep. of Germany | 549/290 |
| 1193512 | 5/1965 | Fed. Rep. of Germany | 549/290 |

OTHER PUBLICATIONS

Korte et al., Tetrahedron 1959, vol. 6, pp. 201–216.

Primary Examiner—Jane T. Fan
Attorney, Agent, or Firm—Leydig, Voit & Mayer

[57] ABSTRACT

A method for making a bicyclic lactone comprising heating under aqueous acidic conditions a beta, gamma unsaturated cyclic nitrile and an aldehyde, for a length of time sufficient to convert at least a portion of the reactants to a bicyclic lactone of the formula

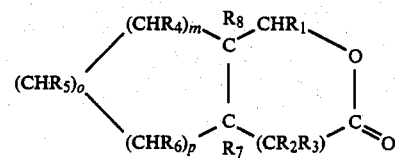

wherein $R_3$ is —H; $R_4$, $R_5$, and $R_6$ are independently selected from the group consisting of —H, —CH$_3$; $R_2$ is selected from the group consisting of —H, —CH$_3$, and —CH$_3$, and —C$_2$H$_5$; $R_8$ is —H or —CH$_3$; m is an integer from 1 to 5; o is 0, 1, 2, or 3; and p is 0, 1, or 2; provided that the sum of m+o+p is an integer from 3 to 5; either $R_3$ or $R_8$ together with $R_7$ represents a carbon-carbon bond. The method uses commercially available and relatively inexpensive raw materials as reactants.

3 Claims, No Drawings

METHOD FOR MAKING BICYCLIC LACTONES FROM BETA, GAMMA UNSATURATED CYCLIC NITRILES

BACKGROUND OF THE INVENTION

This invention is directed to a novel method for making bicyclic lactones.

PRIOR ART

In 1959, several investigators (viz., F. Korte, J. Falbe and A. Zschocke, of the Chemical Institute at Bonn University, West Germany) described (in *Tetrahedron*, published 1959, volume 6, pp. 201–216) a number of methods for synthesizing a variety of bicyclic gamma- and delta-lactones, including the method for synthesizing D, L-Iridomyrmecin. The Tetrahedron article discloses a variety of sequential reaction mechanisms for synthesizing several different kinds or types of bicyclic lactones.

Recently (in 1982) as a result of investigating a particularly surprising physical property possessed by certain bicyclic lactones, it became apparent that need exists for a faster, more economical, and relatively simpler method of synthesizing bicyclic lactones than the methods reported in the Tetrahedron article mentioned above. Further, many of the other published methods of making bicyclic lactones rely in whole or in part on the above-mentioned Tetrahedron article and thus require a number of sequential reactions to produce a bicyclic lactone. (See, e.g., The Merck Index, 10th ed., published 1983, page 734, entry No. 4939.) Thus, as the above-mentioned investigations proceeded, it quickly became apparent that there exists a current need for an efficient method of rapid synthesis of a wide variety of bicyclic lactones. Of course, important considerations of such a method are that it should produce high yields, that the reactants (i.e., starting materials) be relatively available, easy to handle and low in cost, that the number of reaction steps necessary to produce any particular bicyclic lactone be as few as possible, and that reaction parameters (e.g., pressure, temperature and reaction time) be readily achieveable and practical.

OBJECTS AND SUMMARY OF THE INVENTION

It is therefore a general object of this invention to provide a novel method for making bicyclic lactones.

A related object is to provide such a method which permits rapid synthesis, in relatively few steps, of a wide variety of bicyclic lactones.

A more specific object is to disclose a method for synthesizing such bicyclic lactones, which uses commercially available and relatively inexpensive raw materials as reactants.

In accordance with the foregoing objects, a novel method has now been discovered for synthesizing a wide variety of bicyclic lactones, as represented generally by the following structures (Ia) and (Ib)

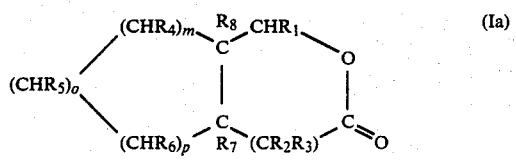 (Ia)

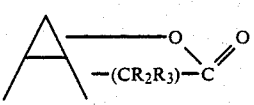 (Ib)

wherein A=represents the group,

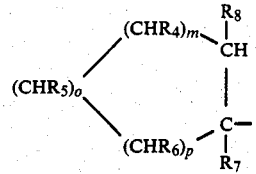

which has had an additional hyrdogen atom removed from a ring-carbon to form a carbon-oxygen bond between said ring-carbon and the oxygen atom in the lactone ring; and wherein each of $R_1$, $R_4$, $R_5$, $R_6$, and $R_8$ are independently selected from the group consisting of —H and —$CH_3$; $R_3$ is —H, $R_2$ is selected from the group consisting of —H, —$CH_3$, and —$C_2H_5$; $R_7$ is hydrogen; or with respect to structure (Ia), either $R_3$ or $R_8$ together with $R_7$ represent a carbon-carbon bond; and wherein m is an integer from 1 to 5; o is 0, 1, 2, or 3; and p is 0, 1, or 2; provided that the sum of m+o+p is an integer from 3 to 5.

When the desired lactone is represented by formula (Ib) above, the method of the present invention comprises heating under aqueous acidic conditions a beta,-gamma-unsaturated cyclic nitrile having the formula (II),

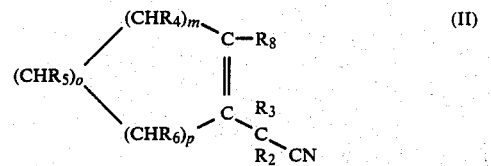 (II)

wherein $R_2$, $R_3$, $R_4$, $R_5$, $R_6$, $R_8$, m, o and p are as defined above, to form the desired bicyclic lactone. When the desired lactone is represented by Formula Ia above, an aldehyde having the formula (III),

 (III)

wherein $R_1$ is as defined above, is employed as an additional reactant.

The present method can be performed easily, quickly and in relatively high yield.

The foregoing objects, as well as other objects, features and advantages of the present invention will become more readily understood upon reading the following detailed description of the preferred embodiments.

DETAILED DESCRIPTION OF THE EMBODIMENTS

While the invention will be described in connection with preferred embodiments, it will be understood that it is not intended to limit the invention to these embodiments. On the contrary, it is intended to cover all alternatives, modifications and equivalents as may be included within the spirit and scope of the invention as defined by the appended claims.

As discussed, it has now been discovered that certain cyclic unsaturated nitriles can produce relatively high yields of bicyclic lactones, under the conditions of the present invention.

The unsaturated nitriles used in accordance with the present invention can be obtained directly or can be prepared using a variety of well known methods of chemical synthesis. For example, by reacting activated-methylene compounds having such activating groups as nitro or carboxylic acid groups, or derivatives thereof (e.g., ester, anhydrides, amides, nitriles, etc.), with ketones or aldehydes, an unsaturated nitrile, or a compound which can be modified via hydrolysis and/or decarboxylation into an unsaturated nitrile, can readily be produced as a primary reaction product. Alternatively, saturated nitrile precursors may be used to obtain the corresponding unsaturated cyclic nitrile compounds, as by using Classical methods of removing $H_2$, $H_2O$, HCl, HOR, etc. moieties to produce the desired unsaturated nitriles, such as described by Korte in Methodicum Chimicum, Georg Thieme Verlag, Stuttgart, 1974 and in Houben-Weyl, Methoden d. Organischen Chemie, George Thieme Verlag Stuttgart, 1963.

Further, other usable precursors of unsaturated nitriles, useful in accordance with the present invention, include the corresponding amides, carboxylic acids or oximes which can be converted into nitriles, or by the procedures described in Methoden d. Organischen Chemie, referenced above, as well as nitrile compounds containing triple bonds, which can be partially hydrogenated, as discussed in Advanced Organic Chemistry, McGraw Hill Kogakusha, 1977, pages 678, 707, 835 and 931, or double bonds (in distinct positions) which can be isomerized by basic or acidic catalysts, as discussed in the above mentioned Methoden d. Organishen Chemie.

Still further, preparation of unsaturated nitriles, in accordance with the present invention, also contemplates reaction of substituted allylic halogens with cyanide.

Thus, as an alternative to beginning with an unsaturated nitrile, a reaction sequence, in accordance with the present invention, can be used, which comprises reacting a cyclic ketone of the formula

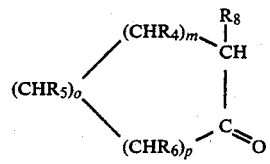

with an α-cyano acid of the formula

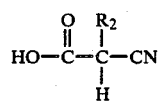

wherein $R_2$, $R_4$, $R_5$, $R_6$, m, o and p are as defined above, in an appropriate solvent containing a suitable catalyst to produce the desired cyclic unsaturated nitrile of Formula II above. The reaction overall can be represented by the following equation (I)

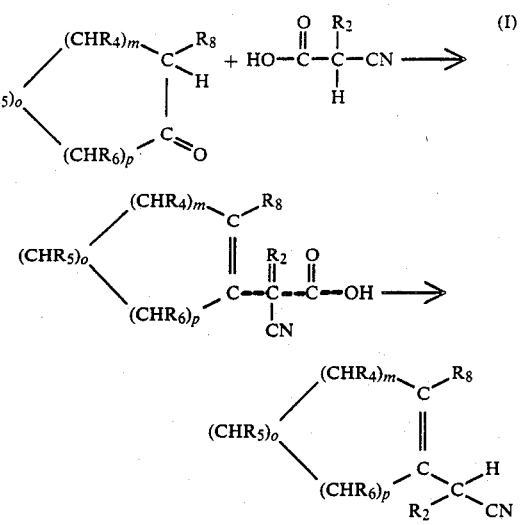

The overall process as shown by Equation I is typically performed in practice by first heating the cyclic ketone with the α-cyano acid in a suitable solvent such as a mixture of acetic acid and benzene, and in the presence of a suitable catalyst, such as ammonium acetate, under substantially anhydrous conditions, generally with water being separated from the reaction mixture, as by refluxing and using a reflux condenser and a water separator. After a sufficient reaction period the reaction mixture can be cooled and the desired intermediate product separated therefrom, which will be the corresponding cycloalkenyl cyano acid, having the formula

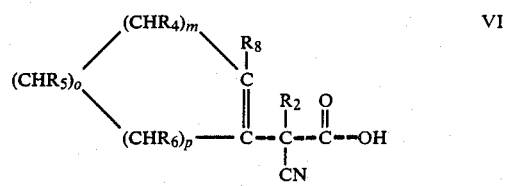

The cycloalkenyl cyano acid is then subjected to decarboxylation, as by using heat and vacuum conditions to obtain the desired unsaturated nitrile of formula II. The nitrile can thus be obtained by vacuum distillation or by simply subjecting the cycloalkenyl cyano acid to heat and vacuum conditions without distillation.

In most instances the beta, gamma-unsaturated cyclic nitrile of formula (II) above will have one of the following structures (IIa), (IIb), or (IIc)

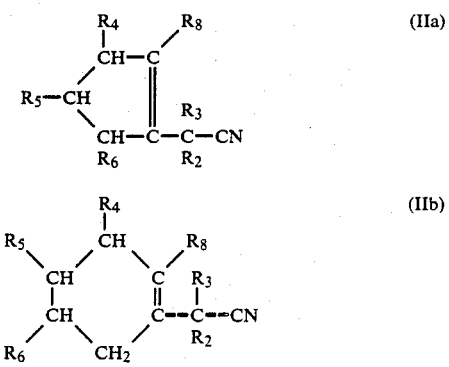

-continued

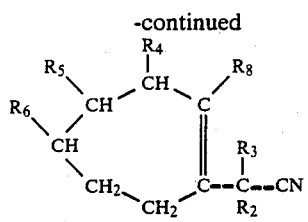
(IIc)

wherein $R_2$, $R_3$, $R_4$, $R_5$, $R_6$ and $R_8$ are as defined above.

After obtaining or synthesizing the unsaturated, cyclic nitrile, the next step depends upon the particular bicyclic lactone which is desired. When the desired product is that shown by structure Ia above, the process comprises reacting the unsaturated nitrile, as shown by structure II above and as obtainable by the foregoing reaction (I), with an aldehyde of structure III above, in an appropriate solvent containing a suitable catalyst. In such an instance, the nitrile, aldehyde and product can typically be represented as shown in Equation II below

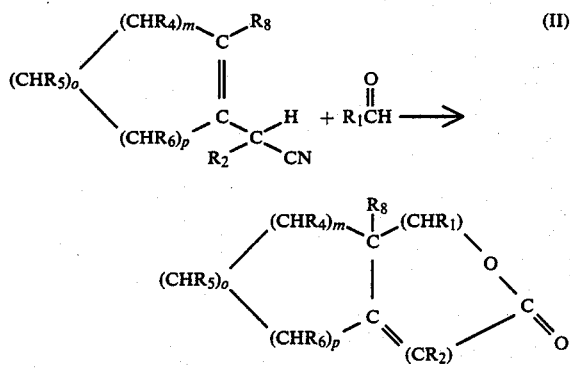
(II)

In the reaction represented by Equation II, any suitable solvent and catalyst can be used, ethylacetate and hydrogen chloride being typical. The reaction can also be carried out with a variety of other acid/solvent combinations. For example, acids such as $H_2SO_{n1}$ wherein $n_1 = 3$ or 4), or $CX_1H_{3n2}COOH$ (where $X_1 = Cl$ or F) (and where $n_2 = 0-3$), or para-toluene sulphonic acid, or $HX_2$ (where $X_2 = Br$ or I), or $HClO_{n3}$ where $n_3 = 3$ or 4), or $HBrO_{n4}$ (where $n_4 = 3$ or 4), or $HIO_{n5}$ (where $n_5 = 3$ or 4), or Lewis acids such as $AlCl_3$, $ZnCl_2$ or $BF_3$, including combinations of these, can be used.

Further, useful solvents having a polarity which is slightly less than, equal to, or greater than that of ethyl acetate, for example ethers (such as dioxane, tetrahydrofuran, glycolmonoether and glycoldiether, and diglycol ether or triglycol ether or polyglycol ether) or alcohols (such as methanol, ethanol, normal-propanol or isopropanol, normalbutanol or isobutonal or tertiarybutanol, and a variety of other higher-boiling alcohols) or acids (such as formic acid, acetic acid, monohalogenated, e.g. fluorine or chlorine, acetic acid or $H_3PO_4$) or other well-known solvents (such as dimethyl formamide, dimethyl sulfoxide), for example, which fulfill the requirements discussed above, have also proved useful in the practice of the invention.

The concentration of either solvent or acid can vary from 0.1 to 99%, and pressure can be varied from 1 to 100 atmospheres.

As the products shown by Equation II are unsaturated, it is readily possible to hydrogenate such compounds to form their hydrogenated counterparts. Such a reaction is shown by Equation III below

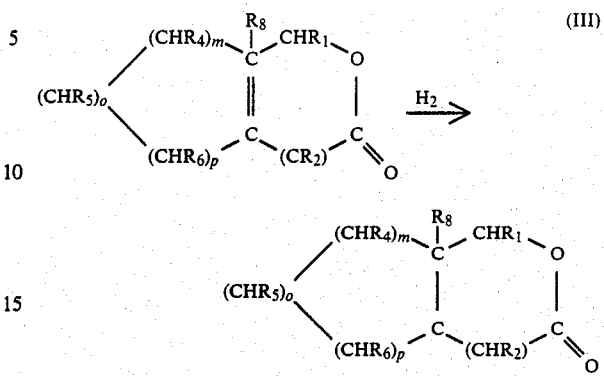
(III)

When the desired bicyclic lactone is that shown by structure (Ib) above, the process of the present invention comprises heating the unsaturated nitrile as shown by structure II above (and as obtainable by the aforementioned reaction step (I)) under acidic conditions in the presence of a suitable catalyst and solvent. In such an instance, the nitrile, and product can typically be represented as shown by Equation IV below

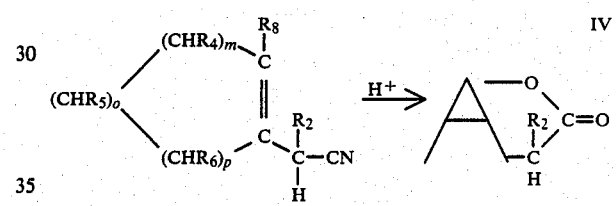
IV

It should be appreciated, of course, that the structure of the bicyclic lactones shown in Equation IV may vary due to structural isomerization. Thus, the lactone ring itself may form between a first ring carbon which is the ring carbon atom on which the nitrile-containing side chain was attached and any other ring carbon which may lose a hydorgen atom to produce an available site.

Thus, in the structure above, A = represents the ring

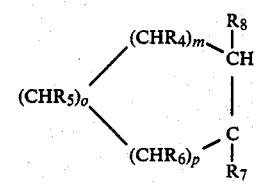

from which a hydrogen atom on a ring carbon has been removed to form a bond between that ring carbon atom and the oxygen atom in the lactone ring. As the lactone need not be a gamma-lactone and may be, for example, a delta lactone, the resulting lactones may have various structures depending upon reaction conditions and the like. To indicate the location of the carbon-oxygen bond on the ring, as used in describing the products of the examples below which have the structure (Ib), the number of the ring carbon atom having said bond will be indicated. Thus, the ring carbon atom to which $R_8$ is attached and which also forms a part of the lactone ring will be designated as number 1 and the remaining carbon atoms in the original nitrile ring will be numbered sequentially in a clockwise manner.

To illustrate the foregoing, in one particular example of the present invention the compound CIC 24 discussed below is manufactured via a reaction which can be represented as follows,

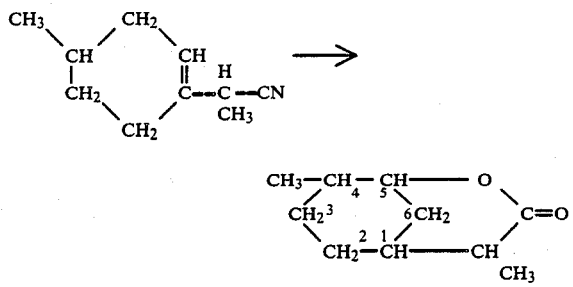

for which n would be assigned the number 5 to identify the ring carbon atom to which the oxygen atom of the lactone ring is attached. Thus, in said reaction $R_4=H$, $m=1$, $R_5=CH_3-$, $o=1$, $R_6=H$, $p=2$, and $R_8=H$.

In the context of the present invention, it is preferred to start with beta-gamma unsaturated nitrile compounds, because no isomerization is necessary for their use in the present invention.

The aldehyde employed in the present process is either formaldehyde or acetaldehyde and can be employed as such or a typical source of such aldehydes can be used in lieu thereof. Thus, paraformaldehyde or trioxane may be used as the source of formaldehyde and metaldehyde may be used as the source of acetaldehyde, in the invention.

Throughout this application, the bicyclic lactones synthesized in accordance with the method of the instant invention are referred to as "CIC" compounds which, in turn, are defined as follows. CIC 2 is 2-hydroxymethyl-3-methyl cyclopentyl-alpha-propionic acid lactone. CIC 3 is 2-hydroxymethyl cyclohexyl-alpha-propionic acid lactone. CIC 4 is 2-hydroxymethyl cyclohexyl acetic acid lactone. CIC 5 is 2-hydroxymethyl cyclohexylidene-alpha-propionic acid lactone. CIC 6 is 2-hydroxymethyl cyclopentyl acetic acid lactone. CIC 7 is 2-hydroxymethyl cyclohexylidene acetic acid lactone. CIC 8 is 2-hydroxymethyl cyclopentyl-alpha-propionic acetic acid lactone. CIC 9 is 2-hydroxymethyl cyclopentylidene acetic acid lactone. CIC 10 is 2-hydroxymethyl cyclopentylidene-alpha-propionic acid lactone. CIC 11 is 2-hydroxymethyl-3-methyl cyclopentylidene-alpha-propionic acid lactone. CIC 12 is 2-hydroxymethyl cyclohexylidene-alpha-butyric acid lactone. CIC 13 is 2-hydroxymethyl cyclopentylidene-alpha-butyric acid lactone. CIC 14 is 2-(1-hydroxyethyl) cyclohexylidene acetic acid lactone. CIC 15 is 2-(1-hydroxyethyl) cyclohexylidene-alpha-butyric acid lactone. CIC 16 is 2-(1-hydroxyethyl) cyclohexylidene-alpha-propionic acid lactone. CIC 17 is 2-(1-hydroxyethyl) cycloheptylidene-alpha-propionic acic lactone. CIC 18 is 2-(1-hydroxyethyl) cyclopentylidene acetic acid lactone. CIC 19 is 2-(1-hydroxyethyl) cycloheptylidene acetic acid lactone. CIC 20 is 2-hydroxy cyclohexyl-alpha-propionic acid lactone. CIC 21 is 2-hydroxy-4-methyl cyclohexyl-alpha-propionic acid lactone. CIC 22 is a mixture of 2-hydroxy-3-methyl cyclohexyl-alpha-propionic acid lactone and 2-hydroxy-5-methyl cyclohexyl-alpha-propionic acid lactone. CIC 23 is 3-hydroxy cyclohexyl-alpha-propionic acid lactone. CIC 24 is 3-hydroxy-4-methyl cyclohexyl-alpha-propionic acid lactone. CIC 25 is a mixture of 3-hydroxy-3-methyl cyclohexyl-alpha-propionic acid lactone and 3-hydroxy-5-methyl cyclohexyl-alpha-propionic acid lactone. CIC 26 is 2-hydroxymethyl cycloheptyl-alpha, alpha-dimethyl acetic acid lactone. CIC 27 is 2-hydroxy cyclohexyl acetic acid lactone. CIC 28 is 2-hydroxymethyl cycloheptylidene-alpha-butyric acid lactone. CIC 29 is 2-(1-hydroxyethyl) cycloheptylidene acetic acid lactone. CIC 30 is 2-hydroxy cycloheptyl acetic acid lactone. CIC 31 is 2-hydroxy cyclopentyl acetic acid lactone. CIC 32 is 2-hydroxymethyl cyclohexenyl acetic acid lactone. CIC 33 is 2-hydroxymethyl cycloheptenyl-alpha, alpha-dimethyl acetic acid lactone. CIC 34 is 2-hydroxymethyl-4-methyl cyclohexylidene acetic acid lactone. CIC 35 is 2-hydroxymethyl-4-methyl cyclohexylidene-alpha-butyric acid lactone. CIC 36 is a mixture of 2-(1-hydroxymethyl)-6-methyl cyclohexylidene acetic acid lactone and 2-(1-hydroxyethyl)-2-methyl cyclohexylidene acetic acid lactone. CIC 37 is a mixture of 5, 6-dimethyl-2-hydroxy methyl cyclohexylidene acetic acid lactone and 2, 3-dimethyl-2-hydroxy methyl cyclohexylidene acetic acid lactone. CIC 38 is a mixture of 3, 5-dimethyl-2-hydroxymethyl cyclopentylidene acetic acid lactone and 2, 4-dimethyl-2-hydroxymethyl cyclopentylidene acetic acid lactone.

Although not presented in Table I (below) other "CIC" compounds, also referred to in this application, are defined as follows. CIC 39 is 2-hydroxymethyl cyclohexylidene acetic acid. CIC 40 is 2-methyl cyclohexylidene acetic acid. CIC 41 is 2-hydroxymethyl cyclohexyl acetic acid. CIC 42 is 2-hydroxy cyclohexyl acetic acid. CIC 43 is cyclohexyl acetic acid. And, CIC 44 is 2-amino cyclohexyl acetic acid latame.

Bicyclic lactone compounds, which were synthesized in accordance with the present invention, are presented below in Table I. Further, physical properties of these "CIC" compounds (i.e., boiling point pressure and temperature) as well as yields employing the present invention are listed in Table I.

TABLE I

Table of Prepared Lactones*

|  | $R_1$ | $R_2$ | $R_3$ | $R_4$ | $R_5$ | $R_6$ | $R_7$ | $R_8$ | m | n | o | p | q | (bp °C./torr) | yield (%) |
|---|---|---|---|---|---|---|---|---|---|---|---|---|---|---|---|
| CIC 2 | H | Me | H | Me | H | — | H | H | 1 | — | 2 | 0 | 1 | 82/0.3 | 58 |
| CIC 3 | H | Me | H | H | — | — | H | H | 4 | — | 0 | 0 | 1 | 82/0.001 | 62 |
| CIC 4 | H | H | H | H | — | — | H | H | 4 | — | 0 | 0 | 1 | 78/0.01 | 45 |
| CIC 5 | H | Me | —H | H | — | — | —H | H | 4 | — | 0 | 0 | 1 | 98/0.3 | 58 |
| CIC 6 | H | H | H | H | — | — | H | H | 3 | — | 0 | 0 | 1 | 85/0.1 | 46 |
| CIC 7 | H | H | —H | H | — | — | —H | H | 4 | — | 0 | 0 | 1 | 110/0.1 | 61 |
| CIC 8 | H | Me | H | H | — | — | H | H | 3 | — | 0 | 0 | 1 | 87/0.03 | 42 |
| CIC 9 | H | H | —H | H | — | — | —H | H | 3 | — | 0 | 0 | 1 | 89/0.25 | 58 |
| CIC 10 | H | Me | —H | H | — | — | —H | H | 4 | — | 0 | 0 | 1 | 72/0.01 | 60 |
| CIC 11 | H | Me | —H | Me | H | — | —H | H | 1 | — | 2 | 0 | 1 | 81/0.2 | 61 |
| CIC 12 | H | Et | —H | H | — | — | —H | H | 4 | — | 0 | 0 | 1 | 105/0.01 | 53 |

TABLE I-continued

Table of Prepared Lactones*

| | $R_1$ | $R_2$ | $R_3$ | $R_4$ | $R_5$ | $R_6$ | $R_7$ | $R_8$ | m | n | o | p | q | (bp °C./torr) | yield (%) |
|---|---|---|---|---|---|---|---|---|---|---|---|---|---|---|---|
| CIC 13 | H | Et | —H | H | — | — | —H | H | 3 | — | 0 | 0 | 1 | 100/0.1 | 47 |
| CIC 14 | Me | H | —H | H | — | — | —H | H | 4 | — | 0 | 0 | 1 | 120/0.3 | 36 |
| CIC 15 | Me | Et | —H | H | — | — | —H | H | 4 | — | 0 | 0 | 1 | 125/0.3 | 30 |
| CIC 16 | Me | Me | —H | H | — | — | —H | H | 4 | — | 0 | 0 | 1 | 130/0.3 | 33 |
| CIC 17 | Me | Me | —H | H | — | — | —H | H | 5 | — | 0 | 0 | 1 | 145/0.3 | 30 |
| CIC 18 | Me | H | —H | H | — | — | —H | H | 3 | — | 0 | 0 | 1 | 140/0.25 | 34 |
| CIC 19 | Me | H | —H | H | — | — | —H | H | 5 | — | 0 | 0 | 1 | 142/0.4 | 30 |
| CIC 20 | — | Me | H | H | — | — | H | H | 4 | 6 | 0 | 0 | 0 | 105/0.2 | 68 |
| CIC 21 | — | Me | H | H | Me | H | H | H | 1 | 6 | 1 | 2 | 0 | 135/0.1 | 72 |
| CIC 22 | — | Me | H | Me | H | — | H | H | 1 | 6 | 3 | 0 | 0 | 120/0.2 | 75 |
| (mixt. of) | — | Me | H | Me | H | H | H | H | 2 | 1 | 1 | 1 | 0 | | |
| CIC 23 | — | Me | H | H | — | — | H | H | 4 | 5 | 0 | 0 | 0 | 125/0.1 | 18 |
| CIC 24 | — | Me | H | H | Me | H | H | H | 1 | 5 | 1 | 2 | 0 | 128/0.2 | 21 |
| CIC 25 | — | Me | H | Me | $H_2$ | — | H | Me | 1 | 5 | 3 | 0 | 0 | 130/0.25 | 12 |
| (mixt. of) | — | Me | H | Me | $H_2$ | H | H | H | 1 | 3 | 3 | 1 | 0 | | |
| CIC 26 | H | Me | Me | H | — | — | H | H | 5 | 0 | 0 | 0 | 1 | 83/0.2 | 53 |
| CIC 27 | — | H | H | H | — | — | H | H | 4 | 6 | 0 | 0 | 0 | 110/0.01 | 62 |
| CIC 28 | H | Et | H | H | — | — | —H | H | 5 | 0 | 0 | 0 | 1 | 150/0.4 | 48 |
| CIC 29 | Me | H | —H | H | — | — | —H | H | 5 | — | 0 | 0 | 1 | 145/0.3 | 23 |
| CIC 30 | — | H | H | H | — | — | H | H | 5 | 7 | 0 | 0 | 0 | 95/0.01 | 65 |
| CIC 31 | — | H | H | H | — | — | H | H | 3 | 5 | 0 | 0 | 0 | 80/0.005 | 68 |
| CIC 32 | H | H | H | H | — | — | —H | —H | 4 | — | 0 | 0 | 1 | 110/0.5 | 68 |
| CIC 33 | H | Me | Me | H | — | — | —H | —H | 5 | — | 0 | 0 | 1 | 112/0.2 | 64 |
| CIC 34 | H | H | —H | H | Me | H | —H | H | 1 | — | 1 | 2 | 1 | 118/0.3 | 52 |
| CIC 35 | H | Et | —H | H | Me | H | —H | H | 1 | — | 1 | 2 | 1 | 128/0.2 | 60 |
| CIC 36 | Me | H | —H | H | Me | — | —H | H | 3 | — | 1 | 0 | 1 | 135/0.1 | 49 |
| (mixt. of) | Me | H | —H | H | — | — | —H | Me | 4 | — | 4 | 0 | 1 | | |
| CIC 37 | H | H | —H | H | Me | — | —H | H | 2 | — | 2 | 0 | 1 | 140/0.4 | 55 |
| (mixt. of) | H | H | —H | Me | H | — | —H | Me | 1 | — | 3 | 0 | 1 | | |
| CIC 38 | H | H | —H | Me | H | Me | —H | H | 1 | — | 2 | 1 | 1 | 108/0.01 | 46 |
| (mixt. of) | H | H | —H | H | Me | H | —H | Me | 1 | — | 2 | 1 | 1 | | |

*The term "—H" means that the carbon atom to which the "R" moiety is attached is unsaturated (i.e. includes a Carbon—Carbon double bond).

Specific reaction details of the method of the present invention are briefly presented in the following examples.

EXAMPLES

Synthesis of Beta,Gamma-Unsaturated Nitrile 170 grams (2 moles) of cyanoacetic acid, 196 grams (2 moles) of cyclohexanone, 10 grams (0.13 moles) of ammonium acetate, 24 grams (0.4 moles) of acetic acid, and 380 milliliters of benzene were combined in a 2-liter round-bottomed flask equipped with a reflux condensor and a water separator, and the mixture heated (with reflux) for 6 hours. Upon cooling, the volatile compounds were removed in vacuo, and the residue washed with water to give 360 grams (1.8 moles, 90% yield) of cyclohexylidene cyanoacetic acid. The cyanoacetic acid was distilled under a vacuum of 50 Torricellis (torr.) thereby producing 196 grams (1.6 moles, 81% yield based on cyclohexanone, or 90% yield based on cyclohexylidene cyanoacetic acid) of cyclohexenyl acetic acid nitrile, which had a boiling point of between 115°–120° C. at 50 torr. (As an alternative to distilling the cyanoacetic acid under vacuum in the lastmentioned step, another portion of the cyclohexylidene cyanoacetic acid when heated to 140°–150° C. under a vacuum of 50–70 torr. for 2.5 hours was found to be readily convertible to an impure cyclohexenyl acetic acid nitrile.)

Synthesis of Unsaturated Bicyclic Lactones From Unsaturated Nitriles and Aldehydes 100 grams (0.83 moles) of cyclohexenyl acetic acid nitrile, 44 grams (0.49 moles) of trioxane, 300 milliliters (3.12 moles) of concentrated hydrochloric acid, and 300 milliliters of ethylacetate were combined in a 1-liter round-bottomed flask equipped with a reflux condensor, and were refluxed for 200 minutes. Upon being cooled, excess HCl was removed in vacuo, and 500 milliliters of $H_2O$ were added. The aqueous layer was extracted 3 times, each time with 200 milliliters of ethylacetate. The organic layers were combined, dried over $Na_2SO_4$, and the above-identified solvents removed in vacuo. The residue, distilled in vacuo, produced 76.9 grams (0.50 moles, i.e. 61% yield) of 2-hydroxymethyl cyclohexylidene acetic acid lactone (referred to as "CIC 7" herein) (the Chem. Abstracts nomenclature after 1967 being 1, 5, 6, 7, 8, 8a-hexahydro-3H-2-benzopyran-3-one), having a boiling point of 110° C. at 0.1 torr. Also produced was 21 grams (0.17 moles, i.e. 21% yield) of cyclohexenyl acetic acid nitrile.

The product CIC 7, which crystallized in the distillation receiver, was found to have a melting point of 45° C., and further was found to have a recrystallization melting point of 58°–59° C. in hexane.

An alternative method of purification, which involves alkaline hydrolysis, has also proved useful in the practice of the present invention. In particular, the reaction mixture, after being washed with water, can be treated with an aqueous NaOH or KOH solution, resulting in the lactone being present either as the corresponding sodium or potassium salt in the aqueous layer. Acidification of the aqueous layer with 100% excess of 1 Normal $H_2SO_4$ at 40° C. for 40 minutes produces up to a 70% yield of CIC 7.

Using identical procedures, CIC 5, CIC 9 through CIC 19, CIC 28, CIC 29 and CIC 33 through CIC 38 were prepared by using the corresponding substituted cyclopentenyl, cyclohexenyl and cycloheptenyl nitriles with the corresponding aldehyde components as shown in Table I.

Synthesis of Saturated Bicyclic Lactones From Unsaturated Bicyclic Lactones

The saturated compounds were prepared by hydrogenation of the corresponding lactones. In a typical hydrogenation experiment, 55 grams (0.36 moles) of CIC 7, 5 grams of Raney-Nickel, and 200 grams of ethanol were combined in an autoclave and hydrogenated at 80° C. and 100 atmospheres of hydrogen pressure until a constant pressure was achieved in the autoclave, i.e. about 3 hours. Thereafter, the Raney-Nickel was removed by filtration, and the volatile compounds were removed by vacuum. Distillation produced 45 grams (81% yield based on CIC 7) of CIC 4, having a boiling point of 78° C. at 0.01 torr. Again using identical procedures, CIC 2 through CIC 4, CIC 6, CIC 8 and CIC 26 were prepared from the corresponding lactones herein referred to as CIC 11, CIC 5, CIC 7, CIC 9, CIC 10 and CIC 33, respectively.

Synthesis of Bicyclic Lactones From Unsaturated Nitrile Without Aldehyde Component When no aldehyde component was used, the lactones CIC 20 through CIC 25, CIC 27, CIC 30 and CIC 31 were produced.

In another typical experiment employing the method of the present invention, a mixture of 5 grams (41 millimoles) of cyclohexenyl acetic acid nitrile, 5 milliliters of sulfuric acid, and 20 milliliters of glacial acetic acid was heated with reflux for 2 hours, and upon being cooled was poured into 100 milliliters of water. After thorough extraction using ether (i.e. 4 separate 30-milliliter additions of ether), the ether layer was dried over $Na_2SO_4$; the ether was removed in vacuo; and the residue distilled in vacuo; resulting in the production of 3.55 grams (25.4 millimoles, a 62% yield) of CIC 27 having a boiling point of 110° C. at 0.1 torr. The distillation residue was found to consist mainly of CIC 44 (resulting in the production of 0.8 grams, a yield of 13%), obtained by treating the residue with ether.

When concentrated hydrochloric acid was used instead of sulfuric acid in the procedure mentioned above, gamma and delta lactones were formed. Gamma and delta lactones can be separated by using preparative silicagel chromatography which in turn uses hexane/ethyl acetate as the separation element.

Also, using corresponding starting materials, it has been found relatively easy to produce the cycloalkyl acetic, alpha-propionic and alpha-butyric acid lactones listed in Table I.

Synthesis of Derivatives

The versatility of the novel method can be shown by the scope of derivatization of the lactone-type compounds, i.e. isomerization of the double bonds, thereby yielding beta-gamma, gamma-delta or delta-epsilon unsaturated lactones such as CIC 32, an isomer of CIC 7.

For example, one such isomerization mechanism for CIC 7 is as follows. 40 grams (0.26 moles) of CIC 7, 50 grams of potassium hydroxide and 80 milliliters of water were combined and heated in a sealed glass tube at 130° C. for 18 hours. After extraction of the cooled and diluted reaction mixture with carbon tetrachloride, the aqueous layer was acidified and thoroughly extracted with chloroform. The organic layer was dried over $Na_2SO_4$ and concentrated in vacuo. Distillation of the residue produced 35 grams (0.23 moles, a yield of 88%) of CIC 32.

Hydrolysis to gamma-hydroxy or delta-hydroxy carbonic acids (such as CIC 39) was carried out as follows. A mixture of 10 grams (82.6 millimoles) of CIC 7 and 100 milliliters of 1 Normal potassium hydroxide solution was heated at approximately 50° C. for 10 minutes, then subjected to an ice-water bath. Thereafter the ice-cold solution was treated with 100 milliliters of 1 Normal sulfuric acid solution, and extracted thoroughly with ether. Crystallization of the ether-soluble reaction product gave 4.9 grams (29 millimoles, a yield of 35%) of CIC 39 having a melting point of 109° C.

Such a carbonic acid can be hydrogenated to CIC 40. The hydrogenation step was carried out either according to the procedure described above for the preparation of CIC 4 or by using 10% Pd/C as a catalyst at ambient temperature (i.e. 21°-27° C.). Such carbonic acids can also be hydrogenated to CIC 40 or CIC 41. Thus, CIC 27 can be hydrolyzed to form CIC 42 from which other derivatives may be formed, such as CIC 43.

Similarly, the lactones can be converted to lactames of the corresponding delta-amino acids, such as CIC 44, by reaction with ammonia or primary amines, or to hydroxyamides, by reaction with secondary amines can be converted to hydroxyamides.

Further, analogous reaction with thio compounds produces the corresponding thiolactones and derivatives thereof. Still further, the carbonyl group can be converted into an imino group, or a thiono group, by well-known procedures.

While the novel method for the preparation of lactones based on the reaction of unsaturated nitriles has been described with reference to preferred embodiments, it is to be noted that the scope of the instant invention is not limited to such embodiments. On the contrary, alternatives, changes or modifications may become apparent to those skilled in the art upon reading the foregoing description. Accordingly, such alternatives, changes and modifications are to be considered as forming a part of the present invention insofar as they fall within the spirit and scope of the appended claims.

What is claimed is:

1. A method for making a bicyclic lactone comprising heating under aqueous acidic conditions a beta, gamma unsaturated cyclic nitrile of the formula

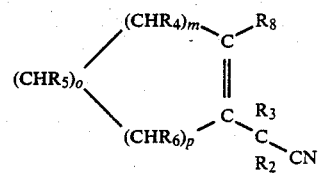

wherein $R_3$ is —H, $R_4$, $R_5$, and $R_6$ are independently selected from the group consisting of —H, —$CH_3$; $R_2$ is selected from the group consisting of —H, —$CH_3$, and —$C_2H_5$; $R_8$ is —H or —$CH_3$; m is an integer from 1 to 5; o is 0, 1, 2, or 3; and p is 0, 1, or 2; provided that the sum m+o+p is an integer from 3 to 5; and an aldehyde having the formula

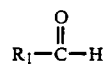

wherein $R_1$ is selected from the group consisting of —H and —$CH_3$, for a length of time sufficient to convert at least a portion of the reactants to a bicyclic lactone of the formula

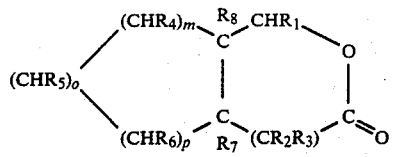

wherein $R_1$, $R_2$, $R_3$, $R_4$, $R_5$, $R_6$, m, o, and p are as defined above, either $R_3$ or $R_8$ together with $R_7$ represents a carbon-carbon bond.

2. The method of claim 1 further comprising the step of hydrogenating said lactone to form a saturated bicyclic lactone of the formula

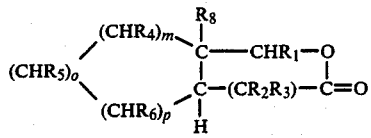

wherein $R_1$, $R_2$, $R_3$, $R_4$, $R_5$, $R_6$, $R_8$, m, o, and p have the meanings defined in claim 1.

3. A method of claim 1 or 2 wherein the unsaturated cyclic nitrile is first obtained by reacting a cyclic ketone of the formula

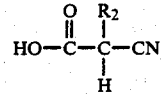

wherein $R_4$, $R_5$, $R_6$, $R_8$, m, o, and p have the meanings defined in claim 1, with an alpha-cyano acid of the formula $$HO-\overset{O}{\underset{}{C}}-\overset{R_2}{\underset{H}{C}}-CN$$

wherein $R_2$ is as defined in claim 1, in an appropriate solvent in the presence of suitable catalyst and under substantially anhydrous conditions to form a cycloalkenyl cyano acid of the formula

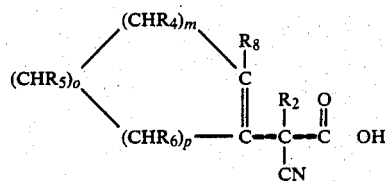

and decarboxylating said cycloalkenyl cyano acid to form the desired unsaturated cyclic nitrile.

* * * * *